(12) United States Patent
Manstein

(10) Patent No.: US 8,274,064 B2
(45) Date of Patent: Sep. 25, 2012

(54) SYSTEM AND APPARATUS FOR DERMATOLOGICAL TREATMENT

(75) Inventor: Dieter Manstein, Miami, FL (US)

(73) Assignee: The General Hospital Corporation, Boston, MA (US)

( * ) Notice: Subject to any disclaimer, the term of this patent is extended or adjusted under 35 U.S.C. 154(b) by 545 days.

(21) Appl. No.: 12/330,252

(22) Filed: Dec. 8, 2008

(65) Prior Publication Data

US 2009/0146086 A1 Jun. 11, 2009

Related U.S. Application Data

(60) Provisional application No. 61/012,238, filed on Dec. 7, 2007.

(51) Int. Cl.
*A61N 5/06* (2006.01)

(52) U.S. Cl. ............... 250/504 R; 250/493.1; 250/503.1; 250/504 H

(58) Field of Classification Search ............... 250/493.1, 250/503.1, 504 R, 504 H
See application file for complete search history.

(56) References Cited

U.S. PATENT DOCUMENTS

| | | | | |
|---|---|---|---|---|
| 3,818,914 A * | 6/1974 | Bender | | 607/90 |
| 4,298,005 A * | 11/1981 | Mutzhas | | 607/94 |
| 4,363,622 A | 12/1982 | Van Laarhoven et al. | | |
| 5,405,368 A * | 4/1995 | Eckhouse | | 607/88 |
| 7,038,227 B2 * | 5/2006 | Aust | | 250/493.1 |
| 7,351,252 B2 * | 4/2008 | Altshuler et al. | | 607/88 |
| 7,722,600 B2 * | 5/2010 | Connors et al. | | 606/9 |
| 2004/0010298 A1 | 1/2004 | Altshuler et al. | | |
| 2004/0010299 A1 | 1/2004 | Tolkoff et al. | | |
| 2004/0087889 A1 * | 5/2004 | Simonsen et al. | | 604/20 |
| 2004/0147986 A1 | 7/2004 | Baumgardner et al. | | |
| 2005/0171581 A1 | 8/2005 | Connors et al. | | |
| 2007/0027440 A1 | 2/2007 | Altshuler et al. | | |
| 2007/0239147 A1 * | 10/2007 | Manstein et al. | | 606/9 |
| 2007/0239236 A1 * | 10/2007 | Manstein | | 607/89 |
| 2009/0166568 A1 * | 7/2009 | Weihs et al. | | 250/504 R |

FOREIGN PATENT DOCUMENTS

| | | |
|---|---|---|
| CN | 1665564 | 9/2005 |
| EP | 0565331 | 10/1993 |
| WO | 2007-002378 | 1/2007 |

OTHER PUBLICATIONS

International Search Report and Written Opinion for Application No. PCT/US2008/085910 dated Jun. 26, 2009.
Communication pursuant to Article 94(3) EPC dated Nov. 7, 2011 for European No. 08860735.3.
Extented European Search report dated Nov. 18, 2010 for European No. 08860735.3.
Chinese Office Action dated May 21, 2012 for CN 200880126238.1.

* cited by examiner

*Primary Examiner* — Michael Maskell
(74) *Attorney, Agent, or Firm* — Dorsey & Whitney LLP

(57) ABSTRACT

Exemplary embodiments of system and apparatus can be provided for treating various dermatological and biological conditions using electromagnetic energy in the form of optical radiation. For example, energy can be provided by a chemical reaction, such as by combustion of a fine metallic filament, which can be used to generate a high-intensity pulse of energy without requiring external energy sources. Various parameters of the reactive materials and enclosures can be selected and/or applied to provide a radiation pulse having particular characteristics, including fluence, peak intensity, and radiation wavelength distribution. Various filters may be provided to further modify characteristics of the radiation. Such radiation pulses can be used to irradiate tissue such as skin to obtain various therapeutic or beneficial effects, including improvement in the appearance of pigmented or venous lesions.

20 Claims, 4 Drawing Sheets

SYSTEM AND APPARATUS FOR DERMATOLOGICAL TREATMENT

CROSS-REFERENCE TO RELATED APPLICATION(S)

This application claims priority to U.S. Provisional Application Ser. No. 61/012,238, filed on Dec. 7, 2007, the entire disclosure of which is incorporated herein by reference in its entirety.

FIELD OF THE INVENTION

The present invention relates to methods and apparatus that use electromagnetic radiation for dermatological treatment and, more particularly to methods, systems and apparatus that use optical radiation generated by a chemical reaction, such as, e.g., in a combustion lamp, to irradiate target sites of skin tissue.

BACKGROUND INFORMATION

There is an increasing demand for repair of or improvement to skin defects, which can be induced by aging, sun exposure, dermatological diseases, traumatic effects, heredity, and the like. Certain treatments may be used to improve skin defects by irradiating the skin with electromagnetic energy, which can lead to beneficial responses to improve the treated skin condition.

In particular, energy provided as optical radiation can be used in a variety of dermatological therapies. Optical radiation can include electromagnetic radiation that has one or more wavelengths in the visible spectrum range, ultraviolet radiation, and/or infrared radiation. Optical radiation can be absorbed by biological tissue, and the amount of such absorption may depend on the wavelength(s) and intensity of the radiation, the characteristics of the tissue and/or particular biological structures or chemical compounds therein, etc. Absorption of optical energy in biological tissue can generate heat and/or disrupt physical structures and/or certain biological functions in the tissue, which may in turn lead to beneficial or therapeutic effects over time.

Dermatological therapies which employ optical radiation can include, for example, removal of tattoos or hair, reducing an appearance of acne, or venous or pigmented lesions such as age spots, angiomas, spider veins, or port-wine stains, as well as wrinkle removal. In these exemplary applications, radiation can be typically delivered from an external energy source and provided to a target region of tissue. Often, it may be preferable to provide such energy as one or more pulses of energy having a large peak intensity and short duration to achieve a desired biological response in the tissue. Energy source which provide such energy can include, e.g., any one of a variety of lasers, electronic flashlamps, etc.

Optical energy may be directed from such energy sources to skin tissue using an optical arrangement such as, e.g., a waveguide or an optical fiber, and may further include one or more lenses, prisms, reflectors, etc. Such optical arrangements can subsequently focus or direct the energy onto the target region of interest. For example, such radiation can be preferentially absorbed by a portion of the skin or hair (e.g., melanin or blood vessels), resulting in localized heating.

A conventional apparatus used to provide energy (e.g., optical radiation) to skin or other tissue in such therapies may include a handpiece or the like, which can be easily repositioned relative to a patient. Such handpiece can be used to direct energy provided by the optical arrangement to one or more specific target regions to be treated.

Conventional methods and apparatus for applying energy to skin tissue as described herein may present many safety issues. For example, energy sources, such as lasers or electronic flashlamps can present a significant risk of overexposure, e.g., directing excessive amounts of energy to tissue and causing unwanted and potentially significant damage to tissue if such energy is not carefully controlled and applied. Safety precautions are often provided when using these exemplary energy sources. For example, an apparatus which includes a laser or other external energy source may often include one or more control arrangements that can regulate, limit, and/or shut off the energy output under certain conditions to reduce a risk of overexposure of skin tissue to the applied radiation. Such arrangements can include, e.g., a pulsing arrangement configured to pulse an energy source instead of providing a continuous energy, which can also prevent overheating of the energy source.

Alternatively, or additionally, a velocity or position sensor associated with a handpiece can be provided to prevent overexposure if such handpiece is translated over a region of the skin to direct energy onto the skin. A feedback arrangement can also be provided to control the energy source, and may be configured to reduce or interrupt an output of energy from the energy source if a dangerous condition is detected. Such feedback arrangement may be based on, e.g., a detected temperature, a reflectivity or other imaging property of the tissue being treated, etc. These safety devices add to the complexity and cost of the various energy application systems.

Conventional energy sources which can be used for such therapies may also require further safety precautions. For example, laser energy sources can require eye protection for operators of the apparatus and/or patients being treated, a limited access to the area where such energy source is being operated, extensive user training, etc. Such energy sources may also present a significant electrical hazard.

Conventional apparatus for providing optical energy to biological tissue may also be expensive, and access to such apparatus may be difficult for certain doctors or other practitioners for economical reasons. Therapies provided using such apparatus may also be costly for patients and/or health insurers. Also, certain apparatus may only be suitable for particular therapies. Thus, it may be impractical for a practitioner to have a variety of such apparatus for providing a range of therapies to patients based on, e.g., economic reasons, limited storage space in a medical facility, etc. Maintenance for such apparatus may also be costly.

Therefore, there may be a need to provide exemplary embodiments of apparatus and methods for application of optical radiation to skin tissue which combine safe, effective and economical treatment for improvement of dermatological defects and other therapies.

SUMMARY OF EXEMPLARY EMBODIMENTS OF THE INVENTION

It is one of the objects of the present invention to provide systems and apparatus which facilitate a safe and economical treatment to improve dermatological defects and other therapies involving application of optical radiation to skin tissue. Another object of the present invention is to provide systems and apparatus which can be used for a range of such therapies, such that a single practitioner may treat a variety of dermatological conditions without requiring a significant financial investment in equipment (e.g., energy sources, handpieces, etc.) and/or significant storage space to house such equipment. It is a further object to provide such exemplary systems and apparatus for treating dermatological conditions which may be safe enough to be used at home by a consumer.

These and other objects can be achieved with the exemplary embodiments of the systems and apparatus according to the present invention, in which a radiation source can be provided that may be configured to generate one or more pulses of optical radiation from a chemical reaction. The radiation source can include a sealed enclosure which contains a reactive material, e.g., a combustible material. The enclosure can be formed of glass, plastic, or another material or combination of materials, such as glass coated with a plastic or polymer. For example, the radiation source can be a combustion lamp or the like. Any reactive material may be used that is capable of producing a sufficiently intense pulse of radiation as described herein when it undergoes a chemical reaction.

The combustible material can be a metal or metal alloy, e.g., aluminum, hydronalium, an aluminum alloy, zirconium, magnesium, or another metal, or a combination of a metal with another substance. The combustible material can be provided in a form of a thin filament or foil to allow rapid reaction, e.g., combustion, of the material. Such rapid reaction can produce a pulse of radiation having a high intensity and a short duration, e.g., on the order of tens of milliseconds or less. A particular atmosphere can be provided within the enclosure to enable or enhance the reaction or combustion. Such atmosphere can include, for example, between about 40% and about 100% moisture-free oxygen, or between about 80% and about 100% moisture-free oxygen.

An exemplary igniting arrangement can also be provided within the enclosure to help initiate the chemical reaction. Such exemplary triggering arrangement can include a primer substance provided, e.g., in contact with two or more electrical contacts that may pass through a wall of the enclosure and are thereby accessible from outside the enclosure.

In certain exemplary embodiments of the present invention, a triggering arrangement may be provided which can include a source of actuation energy and a switch or trigger. The actuation energy can be provided to the igniting arrangement to initiate a chemical reaction within the enclosure. The source of actuation energy can include, e.g., a small battery or energy cell, or a piezoelectric device.

According to further exemplary embodiments of the present invention, a housing can be provided which may be configured to support and/or enclose the combustion lamp or radiation source, and to position such lamp or source at a predetermined distance from the tissue to be treated. Alternative or in addition, the enclosure which contains the reactive or combustible material may also provide such housing.

In still further exemplary embodiments of the present invention, an optical arrangement can be provided to direct the optical radiation produced by the chemical reaction toward the tissue being treated. Such exemplary optical arrangement can include, e.g., a reflective surface or coating provided on at least a portion of the housing or enclosure of the radiation source.

The optical radiation pulse provided by the radiation source can have a duration, e.g., of between about 5 milliseconds and about 200 milliseconds, or between about 10 milliseconds and about 100 milliseconds, or between about 10 milliseconds and about 50 milliseconds. Longer pulse durations may also be provided, e.g., on the order of about one second or longer. Such pulse durations can be provided by selecting properties of the radiation source and combustible material and/or by providing a plurality of radiation sources within a single housing that are activated at different times.

The fluence of optical radiation provided by the radiation source on the tissue being treated may be, e.g., between about 1 $J/cm^2$ and about 30 $J/cm^2$, or between about 1 $J/cm^2$ and about 15 $J/cm^2$. Higher fluence values may also be provided if desired, e.g., by using larger radiation sources, a larger amount of combustible material, directing the pulse of radiation onto a smaller area, etc.

In certain exemplary embodiments of the present invention, one or more filters may be provided to attenuate or block radiation produced by the radiation source that has certain wavelengths or certain ranges of wavelengths. For example, filters can be provided to reduce the amount of ultraviolet and/or infrared optical radiation from impinging on the tissue being treated. Other filters may also be provided to filter out certain wavelengths of radiation in the visible spectrum. Such filters may be provided as separate sheets or plates. Alternatively, portions of the radiation source enclosure and/or housing may be formed using materials that provide such filtering properties.

In certain exemplary embodiments, a water filter may be provided to reduce the amount of infrared radiation produced by the radiation source. Such water filter may be formed as part of the enclosure or housing, or may be attached thereto. The water filter may be cooled or frozen, and thereby provide cooling of the tissue being treated in addition to filtering out some infrared radiation.

In further exemplary embodiments, a plate can be provided which can include one or more apertures that facilitate the optical radiation to pass therethrough and irradiate particular regions of the tissue while preventing other portions of the tissue from being exposed to the radiation. A number of such plates can be provided with apertures of different sizes and/or shapes that can be used to irradiate various lesions, skin defects, etc. having different sizes using a single configuration of the radiation source.

These and other objects, features and advantages of the present invention will become apparent upon reading the following detailed description of embodiments of the invention, when taken in conjunction with the included drawings.

BRIEF DESCRIPTION OF THE DRAWINGS

For a more complete understanding of the present invention and its advantages, reference is now made to the following description, taken in conjunction with the accompanying drawings, in which.

Figure 1:
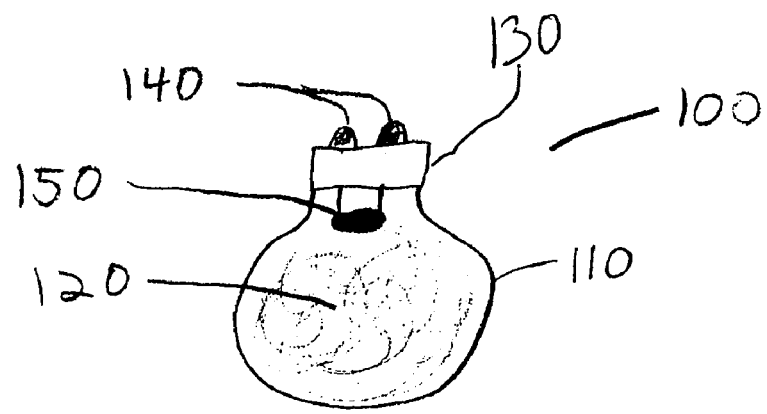
FIG. 1 is an illustration of an exemplary combustion lamp which may be used in accordance with exemplary embodiments of the present invention.

Throughout the drawings, the same reference numerals and characters, unless otherwise stated, are used to denote like features, elements, components, or portions of the illustrated embodiments. Moreover, while the present invention will now be described in detail with reference to the Figures, it is done so in connection with the illustrative embodiments.

DETAILED DESCRIPTION OF EXEMPLARY EMBODIMENTS

Sources of optical energy commonly used in conventional treatment apparatus such as, e.g., a laser, an electronic flashlamp, etc., may be configured to provide a continuous radiation over longer periods of time and/or a plurality of pulses of radiation. Such radiation may be provided by converting the energy obtained directly or indirectly from outside of the energy source such as, e.g., a wall outlet or an electrical generator. For example, a conventional light bulb may shine continuously and thus emit optical radiation when connected to a battery or an electrical outlet. Such optical radiation may not be stored in the light bulb itself, but is converted from electrical energy obtained from outside of the light bulb.

In contrast, exemplary embodiments of the present invention can provide exemplary embodiments of the apparatus and methods for generating and directing particular amounts of optical energy or other radiation onto skin tissue. Such apparatus and methods can include a source of optical energy provided by the apparatus itself through a chemical reaction, e.g., a combustion lamp or flashbulb. Any other chemical system which is configured to produce one or more pulses of optical radiation of sufficient intensity when undergoing a spontaneous reaction, including but not limited to, combustion or oxidation reactions, may also be used in exemplary embodiments of the present invention.

As provided herein, a combustion lamp can refer to a sealed bulb or other enclosure which contains energy stored in a form which can be released using an external stimulus or signal of much lower energy. An example of such combustion lamp can be a conventional photographic flashbulb that may be used to illuminate subjects being photographed. Such combustion lamps can release energy that is stored internally, and a single such lamp may be used once to provide a single pulse of energy. The terms combustion lamp and flashbulb may be used interchangeably herein.

FIG. 1 shows an exemplary illustration of a combustion lamp 100 which may be used in accordance with and/or according to exemplary embodiments of the present invention. For example, the combustion lamp 100 can include an enclosure 110, which can be approximately spherical, or may be provided in another shape. The enclosure 110 can be formed of glass, plastic, or some other material which may preferably allow at least certain wavelengths of radiation to pass therethrough. The enclosure material can be preferably selected to maintain a consistent environment within the enclosure, included any gases provided therein, over extended periods of time. For example, the enclosure 110 may be formed of glass that is coated with a layer of plastic or lacquer that can contain pieces of the glass which may break off or shatter when the combustion lamp 100 is activated and the optical energy is released.

The enclosure 110 can contain a combustible filament 120, which can be made of or include a combustible material such as a metal, e.g., aluminum, hydronalium or another aluminum alloy, another metal, etc. The filament 120 can be provided in a form of a very fine wire and/or very thin foil. The small dimension(s) of the filament 1120 can assist in promoting a rapid reaction of the filament, e.g., an oxidation, and can thereby provide a pulse of optical energy having a short duration or pulse width and high peak intensity. In general, smaller dimensions of the filament 120 (e.g., thinner wire or foil) can lead to longer reaction times and pulse durations, and a lower peak output intensity.

The filament 120 can be formed and/or sealed within the enclosure 110 by a cap 130 or other sealing arrangement. Optionally, the sealing arrangement 130 may be formed as part of the enclosure 110. Before the enclosure 110 is sealed, air can be removed and a particular amount and/or pressure level of moisture-free oxygen can be provided therein. The enclosure 110 can be provided, e.g., with between about 40% and about 100% moisture-free oxygen, or preferably between about 80% and about 100% moisture-free oxygen. Lower levels of oxygen may also be provided for particular filament materials. As described herein, the material of the enclosure 110 may preferably be selected to maintain such gas or gas mixture, including the moisture level thereof, to be relatively constant over extended periods of time. Such consistency in the internal environment of the enclosure 110 can improve the reliability and predictability of performance of the combustion lamp 100.

A plurality of contacts 140 can be provided which may be partially external to the enclosure 110 and the cap 130. The contacts 140 can be in electrical contact with one or more primers 150 sealed within the enclosure 110. The primer 150 can be similar to those used in conventional photographic flashbulbs. A low energy signal can be applied to the contacts 140 to activate the primer 150, e.g., to cause an ignition thereof. Such signal can be, e.g., a voltage which can be provided by a battery, a piezoelectric device, etc. An activation of the primer 150 can initiate a rapid chemical reaction, such as oxidation, of the filament 120 within the enclosure 110, which can release a significant amount of energy from the enclosure 110 in a relative short time.

For example, a pulse of optical radiation produced by activation of an exemplary combustion lamp 100 can have a pulse width, e.g., on the order of tens of milliseconds. Such pulse width or duration can be between, e.g., about 10 milliseconds and about 100 milliseconds, or preferably between about 10 milliseconds and about 50 milliseconds. The pulse duration may also be greater than about 100 milliseconds for certain applications.

Further, a peak intensity of the radiation pulse can also occur on the order of about 20-50 milliseconds after activation of the combustion lamp 100. Such pulse delay observed in a particular combustion lamp 100 can depend on several factors including, e.g., a size of the lamp, an average diameter, width and/or quantity of the filament 120 used, the configuration of the filament 120 within the enclosure 130, the amount of oxygen provided within the enclosure 130, etc. For example, a thicker filament 120 may provide a longer pulse delay because the oxidation of the thicker filament may proceed more slowly as compared with a thinner filament.

Figure 2:
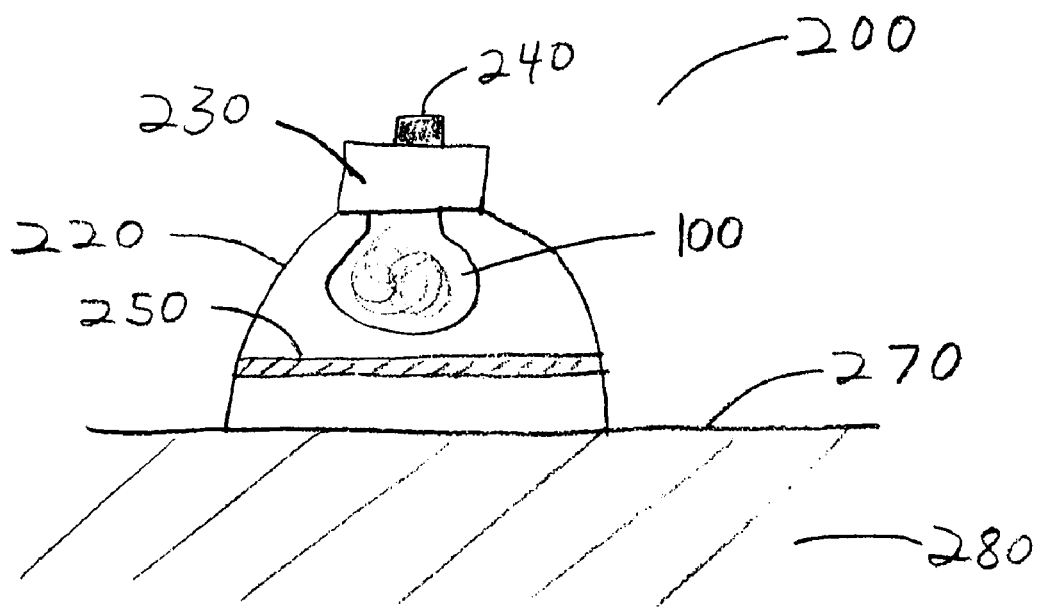
FIG. 2 is n illustration of an exemplary apparatus for providing optical energy to tissue according to exemplary embodiments of the present invention.

An illustration of an exemplary apparatus 200 in accordance with certain embodiments of the present invention is shown in FIG. 2. The exemplary combustion lamp 100 can be provided within a housing 220. An activating arrangement 230 can be provided in connection with the housing 220, and may further be in electrical contact with the combustion lamp 100. The activating arrangement 230 can further include a switch and/or button 240, which when pressed, facilitates an electrical signal to be provided to the combustion lamp 100. The combustion lamp 100 can then release energy stored therein, e.g., as a 'flash' or short-duration intense pulse of optical radiation.

The exemplary housing 220 can be provided, e.g., in a shape of a bell, a dome, or the like, and can be configured to be placed on or over a surface 270 of a region of skin tissue 280 to be treated. The housing 220 can also include a reflective surface or coating, or other optical arrangement, configured to direct a greater amount of the optical radiation released from the combustion lamp 100 toward skin 280 being treated. Such exemplary optical arrangement can thereby increase the efficiency of a particular combustion lamp 100. The increased efficiency can facilitate a higher intensity and/or fluence of radiation to be provided to the skin tissue 280 by the exemplary combustion lamp 100. Alternatively or in addition, the increased efficiency may facilitate a particular intensity and/or fluence to be provided to the skin tissue 280 by a smaller lamp 100, e.g., a lamp 100 which can contain a smaller amount of combustible material.

The activating arrangement 230 can include, e.g., a small battery, a piezoelectric device, or any other energy source which can be configured to activate the combustion lamp 100. The exemplary apparatus 200 can be provided as a disposable device. Alternatively or in addition, the combustion lamp 100 may be replaceable, such that the housing 220 and/or activating arrangement 230 can be re-used.

In certain exemplary embodiments of the present invention, the apparatus 200 can be provided with one or more optional filters 250. Such filter 250 can be located between the combustion lamp 100 and the skin surface 270. For example, the filter 250 may be provided within the housing 220. Alternatively or in addition, the filter 250 may be located at a lower portion or surface of the housing 220, such that it can contact the surface 270 of the skin 280.

The filter 250 can be configured, e.g., to prevent or partially inhibit optical radiation having certain wavelengths or ranges of wavelengths emitted by the combustion lamp 100 from reaching the portion of skin tissue 280 to be treated. Such wavelengths or wavelength ranges may be selected based on the particular defect or condition being treated.

The filter 250, if provided, can be removable, such that one of several such filters 250, each possibly configured to inhibit transmission of optical radiation having different wavelengths and/or wavelength ranges, may be used within a single housing 220 or a plurality of housings 220, e.g., with a particular type of the exemplary combustion lamp 100. In this manner, the energy output characteristics of a single type of the combustion lamp 100 can be modified or tailored for improved efficacy and/or safety for particular applications.

For example, the filter 250 can be an ultraviolet (UV) filter that may be provided so as to prevent, e.g., most of the optical radiation having wavelengths shorter than about 600 nm, or shorter than about 550 nm, from impinging on the tissue being treated. Such UV filters are often used in conventional phototherapy devices that use a broadband source of optical radiation, such as intense pulsed light sources and/or electronic flashlamps.

The filter 250 can also be configured or structured to attenuate or block at least a portion of the optical radiation produced by the combustion lamp 100 that lies in the infrared range. For example, a water filter may be used to reduce the amount of optical radiation that impinges on the tissue being treated having wavelengths around 900 nm and between about 1100-1300 nm. The water filter can include a shallow enclosure or container, at least partially filled with water, which is provided between the source 100 of optical radiation and the tissue 280 being treated. For example, such water filter can be attached to a lower portion of the housing 220. Such water filters may also be used in certain conventional phototherapy devices that utilize a broadband source of the optical radiation.

Figure 3:
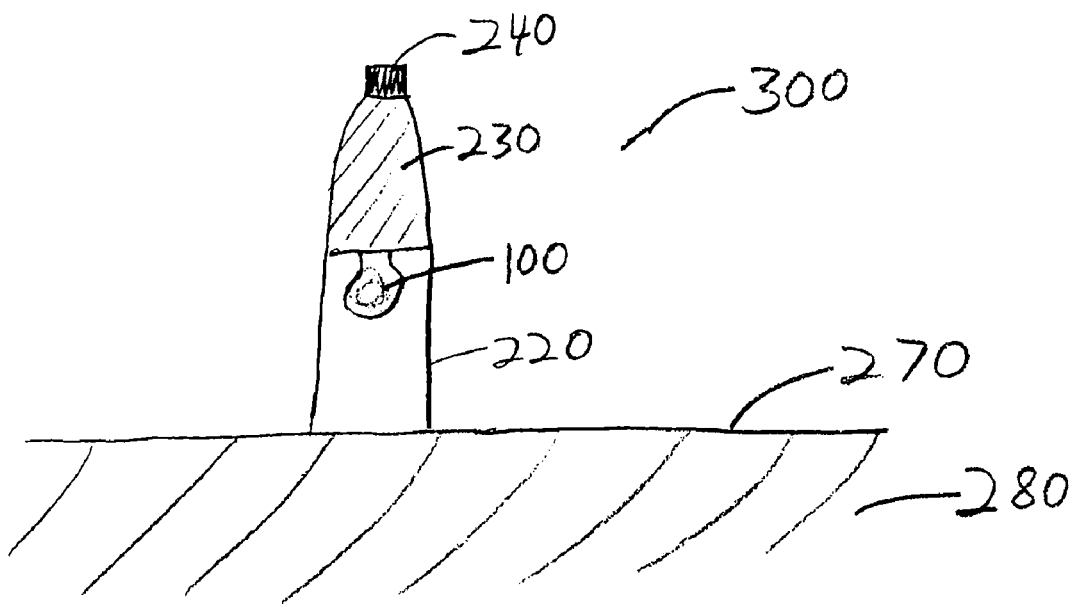
FIG. 3 is an illustration of a further exemplary apparatus for providing optical energy to tissue according to further exemplary embodiments of the present invention.

An exemplary configuration of the exemplary apparatus 300 that may be used in further exemplary embodiments of the present invention is shown in FIG. 3. For example, such exemplary apparatus 300 can include the combustion lamp 100 provided within the housing 220, and the activating arrangement 230 provided in connection with the housing 220. The activating arrangement 230 can further include the switch/button 240 which, when triggered, may cause an electrical signal to be provided to the combustion lamp 100.

The exemplary apparatus 300 may be provided in a shape approximately as shown in FIG. 3, such that it can be easily gripped in a hand and pressed onto a surface 270 of the skin 280 to be treated. In this exemplary configuration, the switch/button 240 may be easily pressed by, e.g., a thumb of a user, while the housing 220 and the activating arrangement 230 are being gripped in the hand. Similar to the exemplary apparatus 200 shown in FIG. 2, a portion of the housing 220 can be provided with a reflective surface or coating to direct optical radiation from the combustion lamp 100 towards the skin 280 to be treated. A variety of such devices 300 can be provided, having a range of shapes, sizes, output properties, filters, etc.

Individual variations of the exemplary apparatus 300 can be tailored for treatment of particular defects or conditions. For example, the exemplary apparatus 300 may be provided with various filters and/or combustion lamps having different energy output for effective treatment of persons having different skin tones. Such variations in specific features for treating different conditions and for different skin types may be provided for any of the exemplary embodiments described herein.

Figure 4:
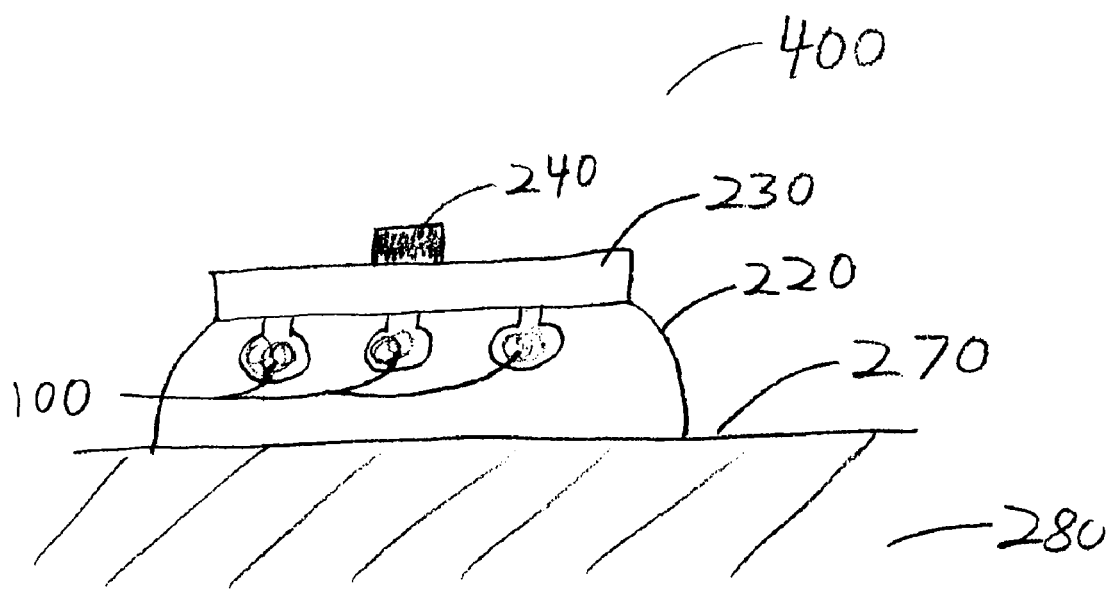
FIG. 4 is an illustration of a still further exemplary apparatus for providing optical energy to tissue according to certain exemplary embodiments of the present invention.

In further exemplary embodiments of the present invention, an apparatus 400 can be provided which includes a plurality of the combustion lamps 100 within the single housing 220, as shown in FIG. 4. For example, the combustion lamps 100 can optionally be connected to the single activating arrangement 230, such that, e.g., each of the combustion lamps 100 can be activated simultaneously by a single button 240. This exemplary configuration can facilitate a higher fluence to the skin tissue 280 than can be achieved using, e.g., a single combustion lamp 100 in the apparatus 200 shown in FIG. 2. The exemplary apparatus 400 can also include a large housing 220, which can provide a particular fluence value to a larger region of the skin 280 as compared to, e.g., the single-lamp apparatus 200 shown in FIG. 2.

The combustion lamps 100 in the apparatus 400 may also be provided with different properties, e.g., different output intensities, emission spectra, filter coatings, etc. Such lamps may also be configured to be activated either simultaneously or sequentially with a predetermined delay to provide particular sequences of optical radiation to the tissue. Although the lamps 100 in FIG. 4 are shown as discrete enclosures, such lamps 100 may be configured as a plurality of separate cavities within a single enclosure.

The activating arrangement 230 can be connected to a single combustion lamp 100, such that only the one combustion lamp 100 is directly activated when the button 240 is pushed. For example, energy released by an activated combustion lamp can further activate a nearby combustion lamp. Thus, the single combustion lamp 100 that is directly activated by the activating arrangement 230 can subsequently activate the other combustion lamps 100 after a brief delay. Such delay may be predetermined, and can be on the order of, e.g., tens of milliseconds, and the amount of delay can further depend on characteristics of the individual combustion lamps 100. In this manner, a longer exposure time of the skin 280 to the radiation provided by the combustion lamps 100 can be achieved by providing more than one such lamp 100 in the single housing 220, and directly activating only certain ones of the combustion lamps 100. In this manner, a temporally extended release of an optical radiation can be provided in a form of a plurality of sequential or non-simultaneous pulses facilitated by a plurality of the combustion lamps 100.

Figure 5A:
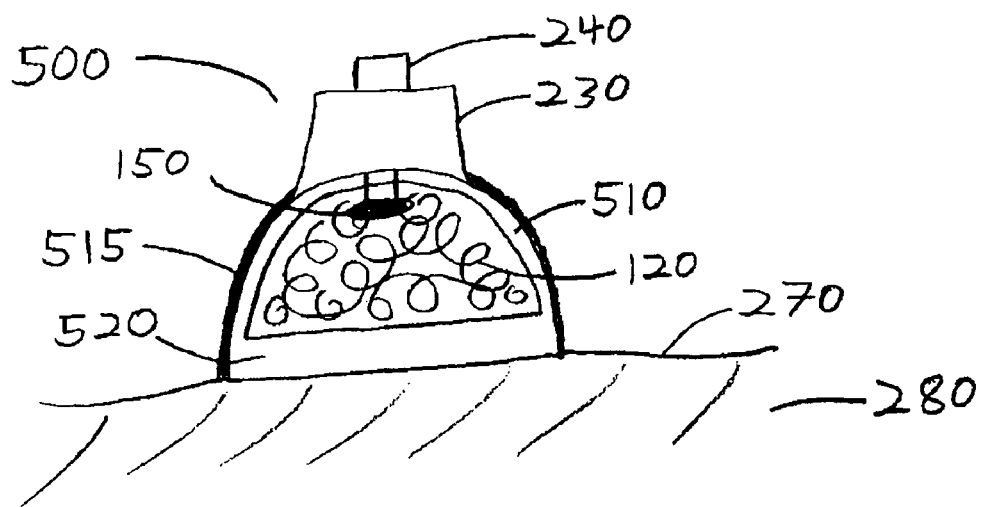
FIG. 5A is an illustration of an exemplary apparatus for providing optical radiation to tissue according to particular exemplary embodiments of the present invention.

An illustration of a still further exemplary apparatus 500 in accordance with further embodiments of the present invention is shown in FIG. 5A. The exemplary apparatus 500 can include lateral walls 510 and a bottom surface 520 which, together, may form an enclosure containing a combustible filament 120 and a primer 150, as described herein. The activating arrangement 230 and the switch 240 can be replaceably or permanently mounted on or in the enclosure. The exemplary apparatus 500 can be used to provide a pulse of the optical radiation to a region of the skin tissue 280 located below the apparatus 500.

The exemplary apparatus 500 can be provided in a bell-like or dome-like shape, as shown in FIG. 5A, which may preferably have an approximately circular shape as viewed from above. Other exemplary shapes may also be used for certain applications. For example, the apparatus 500 may have an ovoid shape or an approximately rectangular shape as viewed from above, e.g., if such shape better conforms to an area of the skin tissue 280 to be treated. The apparatus 500 can be configured to be placed directly in contact with the surface 270 of the skin tissue 280. Thus, the bottom surface 520 of the apparatus 500 may be approximately flat and/or, alternatively, it may be contoured to match a contour of the skin surface 270 in the region of the skin tissue 280 which can receive the optical radiation.

The bottom surface 520 of the exemplary apparatus 500 can be relatively thick, e.g., thicker than the lateral walls 510, such that it may exhibit a large thermal mass. The thick bottom surface 520 may help to protect the skin surface 270 from unwanted thermal damage which could otherwise be caused by heat emitted from the filament 120 when it oxidizes or otherwise reacts to produce the optical radiation. For example, the entire apparatus 500, including the bottom surface 520, can be cooled before being applied to the skin surface 270, e.g., by placing it in a freezer, to further help avoid such unwanted thermal damage. When brought into contact with the surface 270, the cooled bottom surface 520 can also assist in cooling the skin tissue 280 which may also assist in reducing and/or eliminating pain associated with exposure of the skin tissue 280 to the pulse of the optical radiation.

A portion of the side walls 510, e.g., an outer surface thereof, can be provided with a reflective coating or layer 515. As described herein, such reflective coating 515 can direct more of the energy released by combustion or reaction of the filament 120 towards the skin tissue 280 being treated, thus possibly utilizing more of the available energy to irradiate the skin tissue 280.

In certain exemplary embodiments of the present invention, the bottom surface 520 can be formed using and/or be coated with certain materials or additives which can act as a filter to partially or completely block certain wavelengths or wavelength ranges of the optical radiation produced by the filament 120, thereby reducing and/or preventing at least a portion of the radiation having particular wavelengths from passing through the bottom surface 520 and into the skin tissue 280. Similarly, the enclosure 110 of the combustion lamp 100 shown in FIG. 1 may also be formed using materials which have such optical filtering properties. The advantages of such filtering behavior are described herein.

Figure 5B:
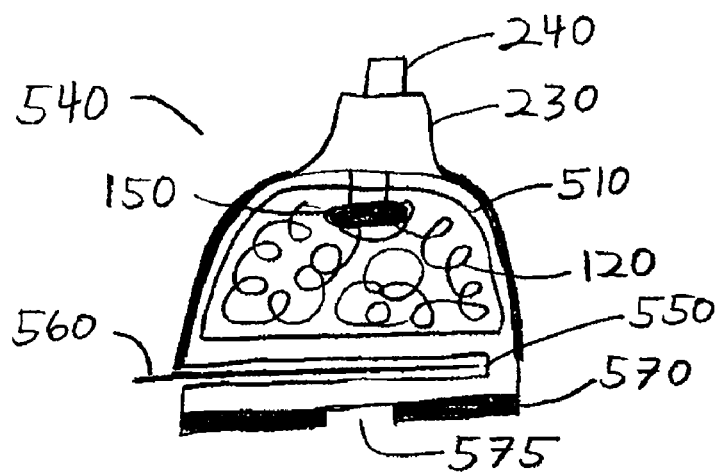
FIG. 5B is an illustration of another exemplary apparatus for providing optical energy to skin tissue according to further exemplary embodiments of the present invention.

Yet another exemplary apparatus 540 in accordance with further embodiments of the present invention is shown in FIG. 5B. The exemplary apparatus 540 is substantially similar to the apparatus 500 shown in FIG. 5A. The exemplary apparatus 540 can be further provided with a slot or aperture 550 in the bottom surface 520. A thin filter 560 can be provided in the slot 550. The thin filter 560 can be used to inhibit or prevent optical radiation having certain wavelengths from impinging on the tissue being treated, as described herein. The filter 560 can be formed of any appropriate material, such as plastic, glass, a gel, etc., which has the desired optical filtering properties. For example, by varying the types of filters 560, the characteristics of the optical radiation produced by the apparatus 540 that impinges on the tissue being treated may be altered to treat different types of conditions or features. The filter 560 may also be an attenuating filter which primarily reduces the peak intensity and/or fluence of the optical radiation which passes therethrough and subsequently interacts with the skin tissue 280.

In certain exemplary embodiments, a plurality of slots or apertures 550 may be provided in the apparatus 540. This exemplary configuration facilitates a plurality of filters 560 to be used to further modify the spectrum of optical radiation wavelengths which pass therethrough and impinge on the tissue being treated. Alternatively or in addition, the slot 550 may be wide enough to accept a plurality of the filters 560 to provide such spectral modification of the optical radiation.

The exemplary apparatus 540 can also be provided with a plate 570 on the bottom surface 520, where the plate 570 can include one or more apertures or openings 575 therethrough. The plate 570 can be used to shield a portion of the tissue below the apparatus 540, such that, e.g., only the tissue below the aperture 575 may be exposed to the optical radiation produced by the apparatus. Accordingly, a single type of apparatus 540 can be used to provide optical radiation to one or more treatment locations located below the aperture(s) 575, while preventing or reducing other nearby regions of the tissue from being irradiated.

The plate 570 may be affixed or fastened to the bottom surface 520 of the apparatus 540. Alternatively or in addition, the plate 570 can be positioned on the surface of the tissue such that the aperture(s) 575 lie directly over the particular areas of tissue to be exposed to optical radiation. The apparatus 540 can then be placed over the positioned plate 570, and actuated as described herein to provide a pulse of the optical radiation through the aperture(s) 575, and directed onto the area(s) of tissue to be treated. A number of such reusable plates 570 having different sizes of apertures 575 can be provided to treat specific areas of tissue having different sizes and/or shapes. Such exemplary plates 570 may also be used with any of the exemplary embodiments of the present invention described herein.

Figure 5C:
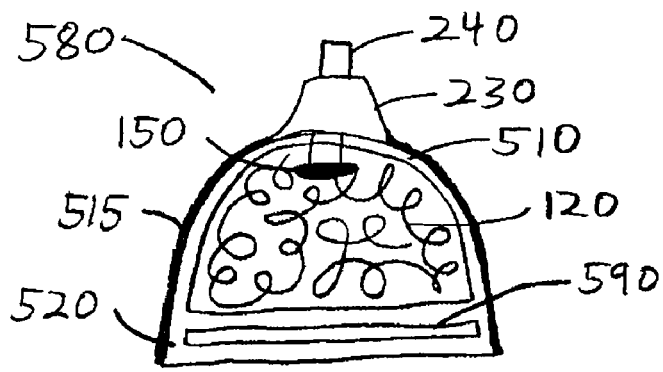
FIG. 5C is an illustration of yet another exemplary apparatus for providing optical energy to skin tissue according to yet further exemplary embodiments of the present invention.

Another exemplary apparatus 580 in accordance with still further embodiments of the present invention is shown in FIG. 5C. The exemplary apparatus 580 is also substantially similar to the apparatus 500 shown in FIG. 5A. The bottom surface 520 of the apparatus 580 can include a cavity 590. The cavity 590 can be filled with water to form a water filter that may reduce and/or eliminate the amount of an infrared radiation passing therethrough as described herein. For example, the exemplary apparatus 580 which includes a water-filled cavity 590 can be stored in a freezer. The frozen water layer can provide both infrared filtering and cooling of the tissue when the apparatus 580 is placed on the tissue to be treated and the optical radiation pulse is generated by activating the combustible material 120. Other materials or mixtures having particular radiation filtering properties may also be provided in the cavity 590. Such materials or mixtures may be solid, liquid, or gaseous in form.

The exemplary apparatus 500, 540, 580 shown in FIGS. 5A-5C, which may not include a separate housing, can be particularly simple and/or inexpensive to manufacture than certain other exemplary configurations which may be provided in accordance with further exemplary embodiments of the present invention.

A safety device may be provided with any of the exemplary systems and apparatus described herein. Such safety device can include, for example, a contact switch or a proximity sensor that is configured to prevent actuation of the radiation source unless the apparatus is placed against or in close proximity to the biological tissue being treated or another surface or object. Such exemplary safety device can facilitate a safer operation of the exemplary systems and apparatus by reducing the likelihood of an accidental or inadvertent triggering of the radiation source.

In accordance with exemplary embodiments of the present invention, combustion lamps having a range of properties can be used. Properties associated with a particular combustion lamp to be used, including those described herein, can be selected based on the particular therapy to be provided and/or particular tissue defect or condition to be treated. For example, properties of several photographic flashbulbs, including, e.g., pulse duration, total output (in lumen-seconds), and peak intensity (in lumens), are described in W. D. Morgan, Syncroflash Photography, Morgan & Lester, New York, N.Y. (1939), 39-54. Combustion lamps having certain exemplary characteristics suitable for particular phototherapy applications may be easily adapted, structured or modified based on the structure of such conventional flashbulbs.

For example, an exemplary pulse duration can be between about 5 milliseconds and about 20 milliseconds for certain applications or, e.g., about 100 milliseconds or longer if desired. Other pulse durations may also be provided, for example, a pulse width of up to about one second. The pulse duration provided by a particular combustion lamp can be based on a width or thickness of the filament 120 (e.g., a metallic wire or foil) provided in the combustion lamp 100. In general, e.g., a thicker filament may lead to a larger pulse width because it can sustain a longer reaction time within the combustion lamp 100. The pulse width may also be affected by, e.g., the particular material used to form the filament 120 and/or the amount of oxygen provided in the enclosure 110.

Certain conventional combustion lamps as described herein can have a color temperature of about 3800° K. The electromagnetic energy in the form of the optical radiation produced by such lamps can thus include a range of wavelengths which lie within the visible spectrum. As described herein, various exemplary filter arrangements can optionally be used to facilitate only certain wavelengths of light emitted by a combustion lamp to irradiate the skin. Such wavelengths may be selected based on several factors such as, e.g., the tissue condition or defect to be treated, the general pigmentation level of a patient's skin tissue, etc.

A particular fluence of radiation applied to a target region of the skin tissue 280 can be determined based on several parameters. For example, the total amount of radiation emitted by the combustion lamp 100 and/or other exemplary apparatus configuration described herein can be varied by changing an amount of the filament 120 provided in the combustion lamp 100. A larger enclosure 110, for example, can facilitate a larger amount of the filament 120 to be provided in the single combustion lamp 100. A plurality of the combustion lamps 100 can be provided in the single housing 220, which can also provide a larger fluence of the skin tissue 280 beneath the housing 220.

Various combustion lamp or enclosure geometries containing the combustible filament 120 or other reactive material can be used for particular applications. For example, instead of a spheroidal shape such as that shown in the combustion lamp 100 of FIG. 1, a wider enclosure such as that shown in FIGS. 5A-5C may be used. The height of such exemplary enclosure may be selected to provide a desired amount of the filament 120 overlying each unit area of the tissue below the apparatus to achieve a particular fluence. The size and shape of such apparatus as viewed from above may also be varied.

For example, the combustion lamp 100 or enclosure 110 may be configured with a small height and relatively wide base, e.g., similar in shape to a thin disc, which provides a relatively small amount of filament (and a correspondingly smaller fluence of optical radiation) over a larger area of tissue. Such exemplary combustion lamp 100 or enclosure 110 may be formed, e.g., using two plates or the like that are separated by a particular distance, with a sidewall joining them along their perimeters. Such exemplary configuration can provide a sealed enclosure that contains a combustible material as described herein, where the height is relatively uniform over its entire area. Accordingly, a relatively uniform fluence of optical radiation can be provided over a particular area of the tissue. The height of such exemplary enclosure may be selected to provide a particular amount of combustible material and a particular fluence when the chemical reaction is initiated. The combustible material can be located relatively close to the tissue in such exemplary configuration, which may further increase the efficiency of the radiation source.

For example, an enclosure or apparatus having a taller enclosure, e.g., greater than about 1-2 cm in height, can provide more of the filament 120 overlying each unit area of tissue, which can generate a larger fluence of the optical radiation when actuated. Conversely, an enclosure having a low profile, e.g., about 1 cm in height or less, may provide, e.g., only a small amount of combustible or reactive filament 120 over each unit area of the tissue. Such low-profile lamp or enclosure may to generate a smaller fluence of optical radiation that can impinge on the underlying tissue.

Factors which can affect the fluence of optical radiation that impinges on the skin can include the geometry of the enclosure, lamp and/or apparatus, the distance between the combustible/reactive material and the tissue being treated, the type and amount of the reactive filament provided therein, reflective surfaces which can direct generated radiation toward the tissue, and any filters placed between the combustion lamp and the tissue. Such exemplary factors can be taken into consideration to generate an appropriate fluence level for particular phototherapy applications.

Exemplary fluence values which may be used for a variety of therapies or skin treatments may generally be selected, e.g., between about 0.5 J/cm$^2$ and about 200 J/cm$^2$, or preferably between about 1 J/cm$^2$ and about 30 J/cm$^2$, or more preferably between about 1 J/cm$^2$ and about 15 J/cm$^2$. Such exemplary fluence ranges may generate varying amounts of heating and/or thermal damage at the skin surface 270 and/or within the skin tissue 280.

Certain exemplary embodiments of the present invention can include a tape, an adhesive, or another fastener which can be used to secure the housing 220 over a region of the skin tissue 280 to be treated. The button 240 and, optionally, the activating arrangement 230 can be provided separate from the housing 220 and the combustion lamp 100. For example, the activating arrangement 230, together with the switch 240, can be provided at some distance from the housing 220, and can be provided in connection to the combustion lamp 100 (e.g., in electrical communication with the primer 150) using, e.g., wires or the like. Alternatively or in addition, the activating arrangement 230 can be affixed to the housing 220 and the switch 240, and may be provided at some distance from the activating arrangement 230 and connected thereto, e.g., using wires or the like.

Exemplary embodiments of the present invention can be used, for example, to treat many defects and provide many therapies to the skin tissue which can include the irradiation of the tissue with optical energy or other electromagnetic radiation. Combustion lamps may be selected or designed to provide an appropriate amount and type of radiation for the desired therapy as described herein. Variation of such parameters as, e.g., combustion lamp size (e.g., the amount of filament 120 contained therein), the size and shape of the housing 220, optional use of the filtering arrangements 250, etc., may be readily determined using calculations or just a few measurements to obtain irradiation parameters suitable for a particular therapy or application.

Various pigmented and/or venous lesions and other dermatological conditions and defects can be treated using the exemplary embodiments of the present invention described herein. Examples of such skin conditions and defects can include, but are not limited to, e.g., age spots (lentigo), acne, port wine stains, hemangiomas, spider veins, removal of unwanted hair, photodynamic therapy, wrinkle removal and collagen shrinkage, etc.

The optical radiation provided by the exemplary embodiments of the present invention described herein may also be combined with various substances to provide more effective treatment of certain conditions. For example, chromophores may be applied to certain portions of the tissue being treated to enhance the absorption of optical radiation. Such chromophores can include, e.g., carbon particles provided in a solution or in a marker pen, or any other conventional chromophore used in phototherapy applications.

In accordance with further exemplary embodiments of the present invention, a radiation-absorbing material may also be provided on, or formed within, a portion of a lower surface of any of the exemplary apparatus described herein. The optical radiation can heat the absorbing material, thereby providing indirect heating of the tissue being treated as well as a fluence of optical radiation. Absorbing materials can include foils, films, gels, etc. which contain chromophores such as, e.g., carbon particles or any other conventional chromophore. Such heating may improve the efficacy of treating certain pigmented lesions such as lentigo (age spots).

Photosensitizers may also be used with embodiments of the present invention to enhance the effects of optical radiation on tissue. Such photosensitizers can be used, e.g., in photodynamic therapy treatments. A lidocaine gel or solution may also be applied to the tissue to help reduce pain sensations and to act as a photosensitizer. In certain exemplary embodiments, a lidocaine gel may be provided on a lower surface of the housing or enclosure, such that the gel contacts the tissue surface when the apparatus is placed on the tissue prior to treatment. Other conventional photosensitizers may also be used with the optical radiation generated by the exemplary systems and apparatus described herein.

A few specific examples of treatments are described in detail. For example, exemplary embodiments of the present invention can be used for a variety of phototherapy treatments that conventionally employ a relatively small number of pulses of radiation.

EXAMPLE 1

Figures 6A, 6B:
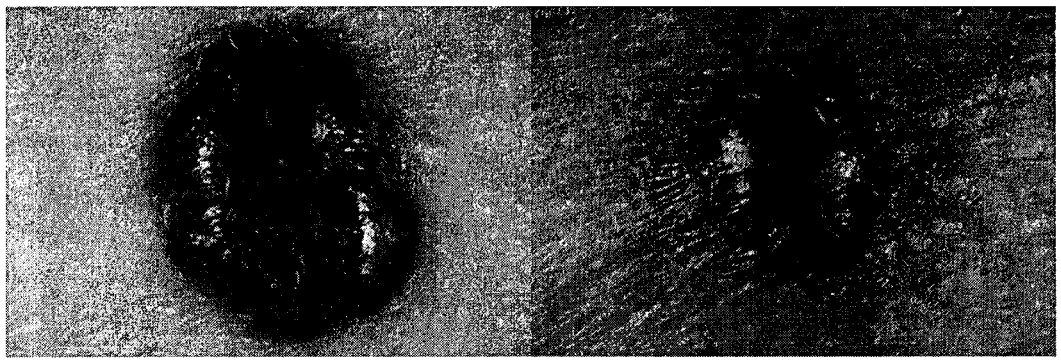
FIG. 6A is an exemplary image of a raised cherry angioma.
FIG. 6B is an image of the cherry angioma shown in FIG. 6A, e.g., six weeks after irradiating it with a single pulse of optical radiation in accordance with an exemplary embodiment of the present invention.

FIG. 6A shows a photograph of a raised cherry angioma that measures about 5 mm across. The angioma was treated in accordance with certain exemplary embodiments of the present invention by exposing it to a single pulse of optical radiation provided by an M3 photographic flashbulb. A reflecting arrangement was provided around the combustion lamp, and no filtering of the optical radiation was used. The radiation was provided through an aperture positioned over the cherry angioma. The fluence of the applied radiation was about 9-10 J/cm$^2$, and the total energy provided in the single pulse was about 4 J. The pulse duration was about 10-15 milliseconds.

Some initial darkening and crusting of the angioma was observed within the first week. The appearance of the angioma about six weeks after treatment is shown in a photograph of FIG. 6B, taken at the same magnification as the photograph shown in FIG. 6A. There appears to be a marked improvement in the appearance of this defect, with an overall lightening of the angioma and a reduction in its size. The appearance may be further improved by application of a second pulse, if desired. Some residual damage to the healthy tissue surrounding the angioma is evident in the photograph of FIG. 6B. Such undesirable effects may be reduced, e.g., by providing an ultraviolet filter as described herein, reducing the fluence of the applied pulse of optical radiation, or a combination of these modifications.

EXAMPLE 2

Figures 7A, 7B:
FIG. 7A is an exemplary image of a flat angioma.
FIG. 7B is an image of the angioma shown in FIG. 7A, e.g., six weeks after irradiating it with a single pulse of optical radiation in accordance with an exemplary embodiment of the present invention.

FIG. 7A shows a photograph of a regular (flat) angioma that is about 4 mm in diameter. This angioma was exposed to a single pulse of unfiltered optical radiation provided by an M3 photographic flashbulb, in accordance with exemplary embodiments of the present invention. A reflecting arrangement was provided around the combustion lamp, and the radiation was provided through an aperture positioned over the angioma. The fluence of the applied radiation was about 9-10 J/cm$^2$, and the total energy provided in the single pulse was about 4 J. The pulse duration was about 10-15 milliseconds.

Some immediate raising and darkening of the angioma was observed, and some crusting of the angioma occurred within the first week. The appearance of the angioma about six weeks after treatment is shown in a photograph of FIG. 7B. The angioma appears significantly lighter and smaller. A small amount of damage to the skin surrounding the angioma is evident in the photograph of FIG. 7B, which may be reduced, e.g., by providing a UV filter for the radiation pulse and/or lowering the applied fluence slightly.

EXAMPLE 3

Figures 8A, 8B:
FIG. 8A is an exemplary image of a brown age spot (lentigo)
FIG. 8B is an image of the age spot shown in FIG. 8A, six weeks after irradiating it with a single pulse of optical energy in accordance with an exemplary embodiment of the present invention.

A brown age spot (lentigo) that measures about 3 mm across, shown in a photograph of FIG. 8A, was treated by exposing it to a single pulse of optical radiation in accordance with exemplary embodiments of the present invention. The unfiltered radiation was provided by an M3 photographic flashbulb situated in a reflective housing. An aperture was positioned over the lentigo. The total fluence of the radiation pulse was about 9-10 J/cm$^2$, and the applied energy was about 4 J. The pulse duration was about 10-15 milliseconds.

Some initial smoothing of the lentigo was observed, and darkening of the lentigo occurred within the first day that faded within about one week. The appearance of the lentigo about six weeks after treatment is shown in a photograph of FIG. 8B. Although not visible in this grayscale image of FIG. 8A, the brownish appearance of the lentigo shown in the photograph of FIG. 8A is significantly reduced, and the darker areas in the photograph of FIG. 8B are more reddish in appearance. The enhanced pigmentation of the lentigo was thus reduced by the present treatment. The dark area shown in FIG. 8A indicates some damage to the skin tissue which occurred in conjunction with the lightening of the pigmented lesion itself. Such auxiliary damage may be reduced, e.g., by providing an infrared filter for the optical radiation pulse and/or reducing the fluence of the applied pulse for such age spots.

It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced herein are incorporated herein by reference in their entireties.

What is claimed is:

1. An apparatus for applying an optical radiation to at least one biological tissue, comprising:
    a sealed enclosure;
    a combustible material provided within the enclosure and configured to generate the radiation based on a chemical reaction; and
    a water filter,
    wherein a portion of an outer surface of the sealed enclosure is configured to contact the biological tissue,
    wherein the water filter is provided between the combustible material and the portion of the outer surface of the sealed enclosure, and is configured to both filter a portion of the optical radiation and cool the biological tissue, and
    wherein the optical radiation produces a biological effect on at least a portion of the at least one biological tissue.

2. The apparatus of claim 1, wherein the water filter comprises a closed cavity provided in a portion of the sealed enclosure.

3. The apparatus of claim 2, wherein the combustible material comprises at least one of aluminum, hydronalium, zirconium, magnesium, or an aluminum alloy.

4. The apparatus of claim 2, wherein the apparatus further comprises a gas containing between about 80% and about 100% moisture-free oxygen provided within the sealed enclosure.

5. The apparatus of claim 2, further comprising a triggering arrangement configured to initiate the chemical reaction, wherein the triggering arrangement comprises a switch and a source of an actuation energy.

6. The apparatus of claim 5, wherein the radiation arrangement further comprises an igniting arrangement provided within the enclosure, and the triggering arrangement is configured to provide the actuation energy to the igniting arrangement to initiate the chemical reaction within the sealed enclosure.

7. The apparatus of claim 5, wherein the triggering arrangement source of energy comprises at least one of a battery or a piezoelectric crystal.

8. The apparatus of claim 2, further comprising an optical arrangement configured to direct at least a portion of the optical radiation toward the at least one biological tissue.

9. The apparatus of claim 8, wherein the optical arrangement comprises a reflective surface.

10. The apparatus of claim 2, further comprising a housing configured to locate the radiation arrangement at a predetermined distance from the tissue.

11. The apparatus of claim 2, wherein the cavity is at least partially filled with water.

12. The apparatus of claim 11, wherein the water filter further comprises at least one further material provided within the cavity, wherein the at least one further material is adapted to filter at least one portion of the optical radiation having particular wavelengths from impinging on the at least one biological tissue.

13. The apparatus of claim 2, wherein the radiation arrangement is configured to provide a pulse of optical radiation, and wherein a duration of the pulse is between about 10 milliseconds and about 100 milliseconds.

14. An apparatus for applying optical radiation to at least one biological tissue, comprising:
    a combustion lamp capable of generating at least one pulse of optical radiation when actuated;
    a reflective surface configured to direct at least a portion of the optical radiation toward the at least one biological tissue; and
    a water filter,
    wherein a portion of an outer surface of the combustion lamp is configured to contact the biological tissue,
    wherein the water filter is provided between the combustible material and the portion of the outer surface of the combustion lamp and is configured to both filter a portion of the optical radiation and cool the biological tissue, and
    wherein a fluence of the radiation produces a biological effect on at least one portion of the at least one biological tissue.

15. The apparatus of claim 14, wherein the combustion lamp comprises a sealed enclosure, and wherein a combustible material and a dry gas comprising oxygen are provided within the sealed enclosure.

16. The apparatus of claim 14, further comprising a triggering arrangement configured to actuate the combustion lamp.

17. The apparatus of claim 15, wherein the water filter comprises a closed cavity provided in a portion of the sealed enclosure that is at least partially filled with water.

18. The apparatus of claim 14, wherein a duration of the at least one pulse is between about 10 milliseconds and about 100 milliseconds.

19. The apparatus of claim 14, wherein, a fluence of the at least one pulse of optical radiation provided on the tissue is between about 1 J/cm$^2$ and about 30 J/cm$^2$.

20. The apparatus of claim 14, wherein the reflective surface is provided on at least one portion of the combustion lamp.

* * * * *